US00PP31821P2

(12) United States Plant Patent
Brand

(10) Patent No.: US PP31,821 P2
(45) Date of Patent: Jun. 2, 2020

(54) ***ARONIA* PLANT NAMED 'UCONNAM012'**

(50) Latin Name: *Aronia melanocarpa*
Varietal Denomination: UCONNAM012

(71) Applicant: University of Connecticut, Farmington, CT (US)

(72) Inventor: Mark Henry Brand, Willington, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 16/501,509

(22) Filed: Apr. 18, 2019

(51) Int. Cl.
*A01H 5/00* (2018.01)
*A01H 6/74* (2018.01)

(52) U.S. Cl.
USPC ..... Plt./156
CPC ..... *A01H 6/74* (2018.05)

(58) Field of Classification Search
USPC ..... Plt./156
CPC ..... A01H 5/00
See application file for complete search history.

*Primary Examiner* — Kent L Bell
(74) *Attorney, Agent, or Firm* — Cassandra Bright

(57) ABSTRACT

A new and distinct *Aronia* cultivar named 'UCONNAM012' is disclosed, characterized by dwarf, dense plants with good ground coverage, and prostrate branching. Foliage is glossy and green throughout the Spring and Summer, turning red in the Fall. The new variety is an *Aronia*, normally produced as an outdoor garden plant.

4 Drawing Sheets

This invention was made with government support under grant numbers 2009-38640-19631 and 2015-31200-06009 awarded by the United States Department of Agriculture National Institute of Food and Agriculture. The government has certain rights in the invention.

Latin name of the genus and species: *Aronia melanocarpa.*

Variety denomination: 'UCONNAM012'.

BACKGROUND OF THE INVENTION

The new *Aronia* cultivar is a product of a planned breeding program conducted by the inventor, Mark Henry Brand in Mansfield, Conn. The objective of the breeding program was to develop a prostrate ground cover form of *Aronia melanocarpa* less than 12" tall with substantial bloom, shiny foliage, black fruit and colorful fall foliage. The cross resulting in this new variety was made during May of 2003. Date of first advertising was Jun. 26, 2018, in Grand Haven, Mich. This was made directly by the inventor or one who obtained information about the claimed invention directly or indirectly from the inventor. This sale and all public disclosures made before the filing of this application fall within the exception allowed under 102(b)(1).

The seed parent is the unpatented variety *Aronia melanocarpa* 'BPMe'. The pollen parent is unknown. The new variety was discovered in May of 2006 by the inventor in a group of seedlings resulting from the 2003 crossing, in a research nursery in Mansfield, Conn.

Asexual reproduction of the new cultivar 'UCONNAM012' by softwood stem cuttings, was first performed during June of 2006, at a nursery in Mansfield, Conn. Subsequent propagation by softwood cuttings has shown that the unique features of this cultivar are stable and reproduced true to type in 4 successive generations.

SUMMARY OF THE INVENTION

The cultivar 'UCONNAM012' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'UCONNAM012' These characteristics in combination distinguish 'UCONNAM012' as a new and distinct *Aronia* cultivar:

1. Prostrate plant form.
2. Dwarf, dense growth.
3. Glossy foliage.
4. Ornamental use during Spring, Summer and Fall.
5. Suitability as a landscape groundcover.

PARENT COMPARISON

Plants of the new cultivar 'UCONNAM012' are similar to plants of the seed parent, *Aronia melanocarpa* 'BPMe' in most horticultural characteristics, however, plants of the new cultivar 'UCONNAM012' differ in the following;

1. The new variety is very prostrate with dense growth, covering the ground thoroughly. The seed parent is prostrate, but not dense.
2. The new variety's foliage is glossy, while the seed parent's foliage is matte to glossy.

COMMERCIAL COMPARISON

Plants of the new cultivar 'UCONNAM012' can be compared to the variety *Aronia* 'UCONNAM165', U.S. Plant Pat. No. 28,789. These varieties are similar in most horticultural characteristics; however, 'UCONNAM012' differs in the following:

1. The new variety is more spreading, ground covering, while this comparator is more compact and mounded.

BRIEF DESCRIPTION OF THE PHOTOGRAPHS

The accompanying photograph in FIG. 1 illustrates in full color a typical plant of 'UCONNAM012' shown in a 3 gallon container in a greenhouse in Grand Haven, Mich.

Figure 1:
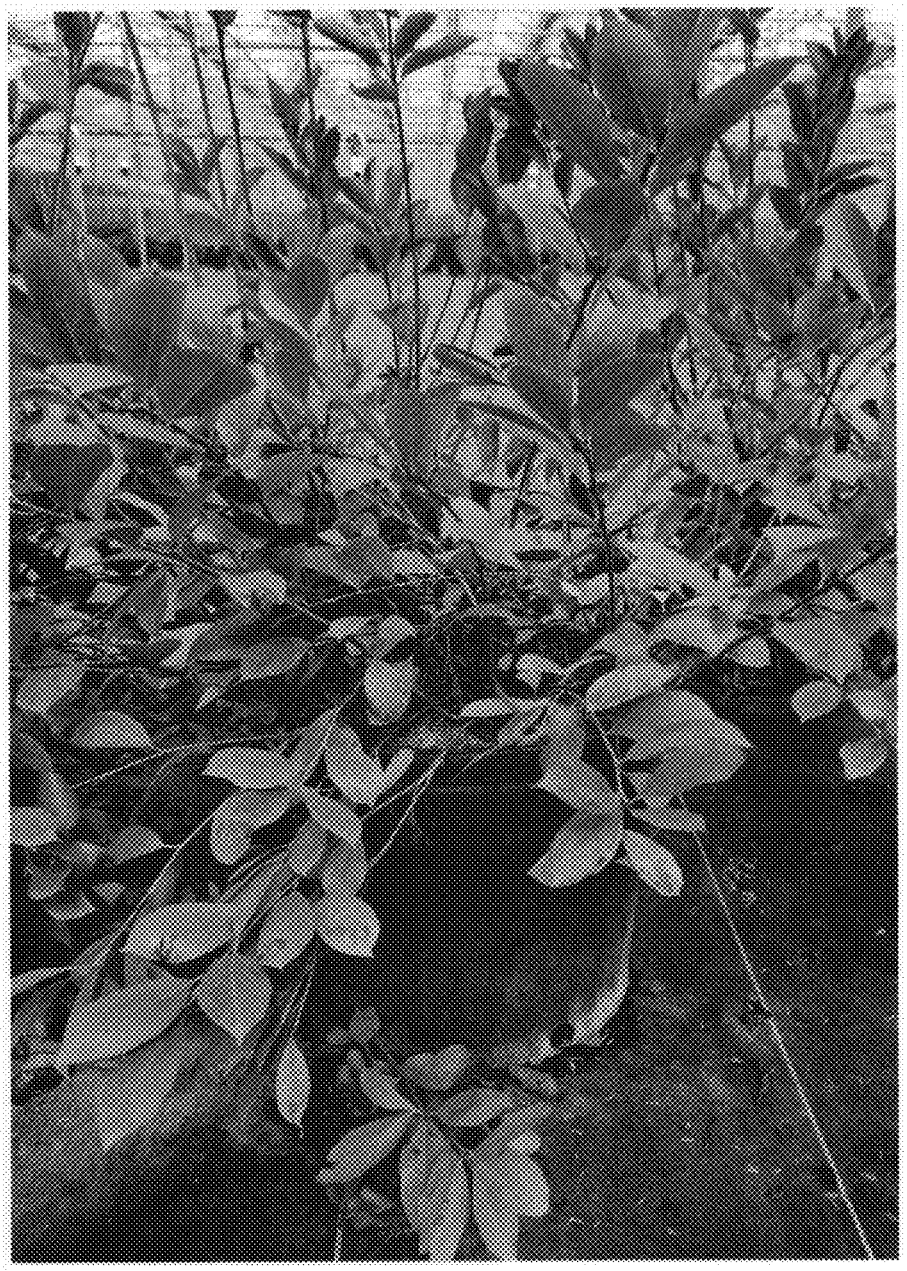
Figure 2:
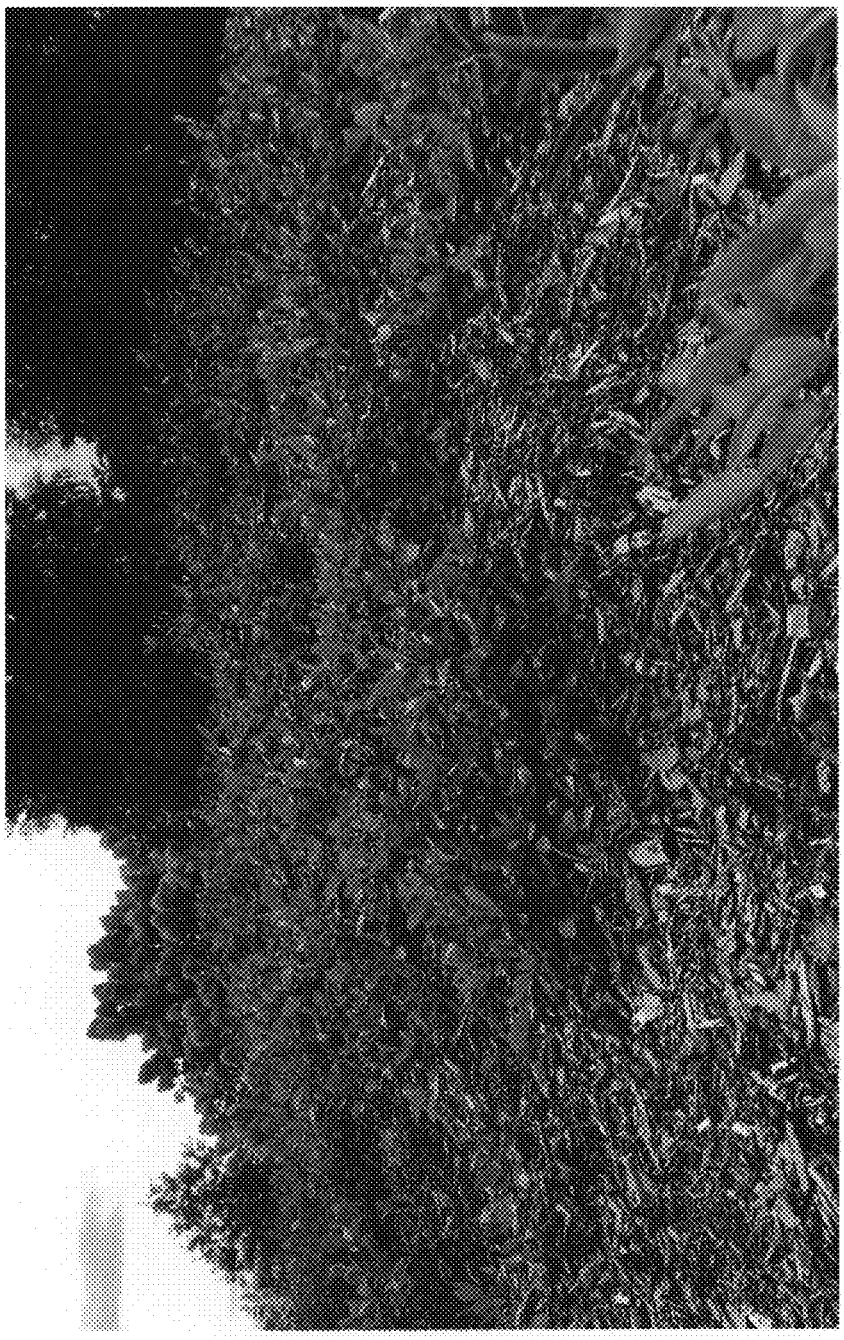
FIG. 2 illustrates in full color the prostrate growth of plants in the ground in an outdoor setting.
Figure 3:
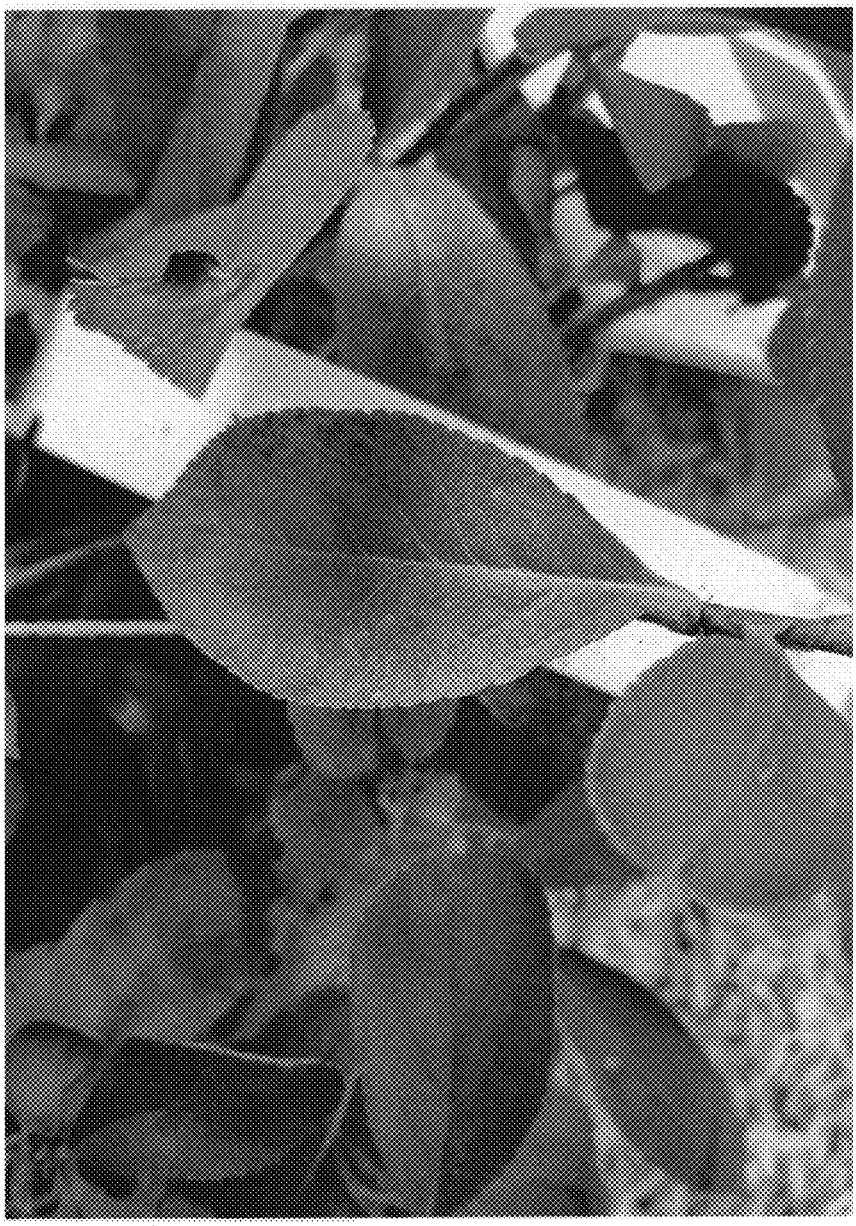
FIG. 3 illustrates a close up of typical foliage beginning to show Fall coloration. inflorescence and foliage of 'UCONNAM012'.
Figure 4:
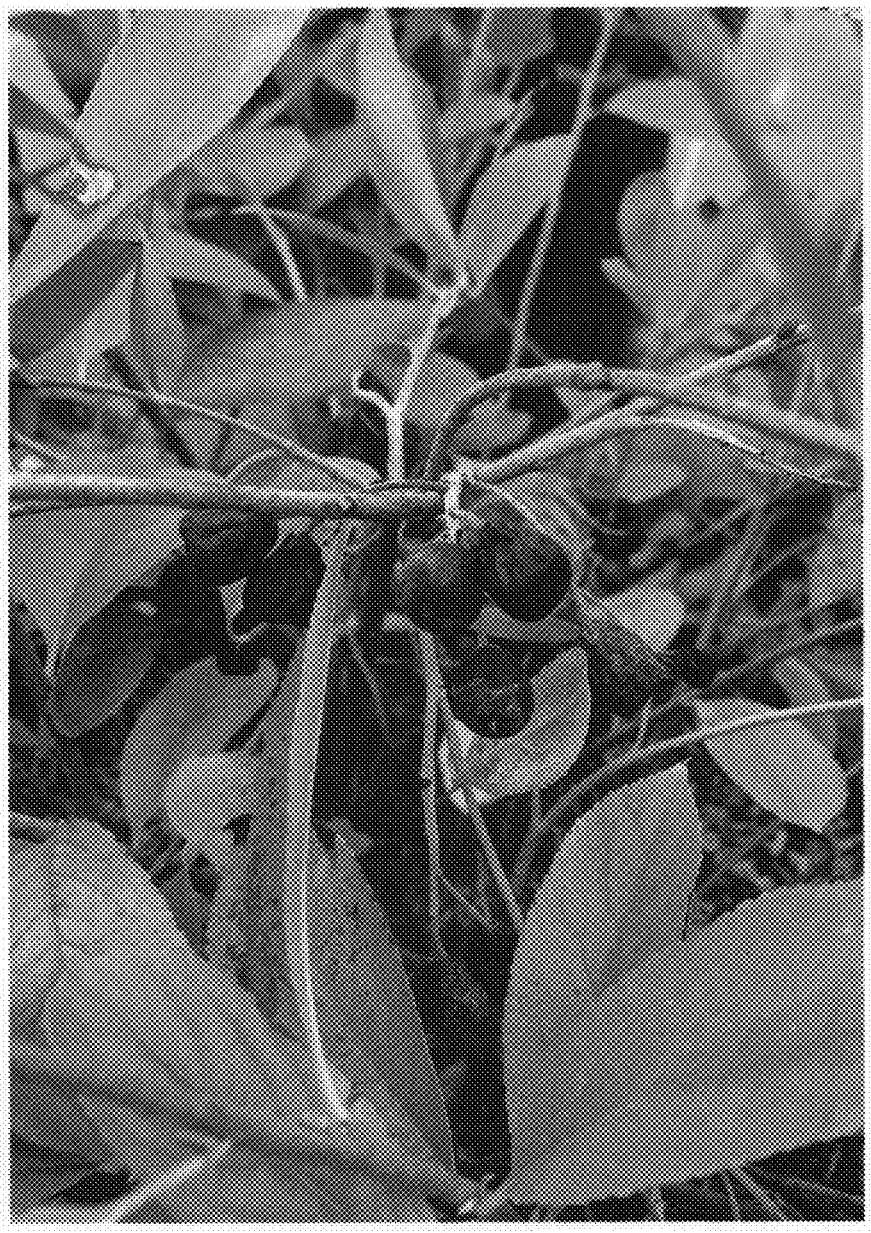
FIG. 4 illustrates fruit and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'UCONNAM012' plants grown in polyhouse in Grand Haven, Mich., under natural lighting. Measurements were taken during Summer of 2018. The plants were 1-2 years old in #3 containers. The growing temperature ranged from 5° C. to 27° C. Measurements and numerical values represent averages of typical plant types.

Botanical classification: *Aronia melanocarpa* 'UCONNAM012'.

PROPAGATION

Time to initiate roots: About 3 weeks at approximately 24° C.

Time to produce a rooted young plant: About 8 weeks at 24° C.

Roots: Moderate density moderate branching. Medium thickness, fibrous and white in color, not accurately measured with The R.H.S. Chart.

PLANT

Plant type: Perennial shrub.

Age of plant described: 1 to 2 years.

Growth habit: Prostrate.

Pot size of plant described: 3 gallon.

Appropriate containers sizes: 1, 2 and 3 gallon nursery containers.

Overall plant shape: Spreading.

Height: 19 cm.

Plant spread: 26 cm.

Growth rate: Good.

Plant vigor: Good.

Branching characteristics: Freely branching.

Length of primary lateral branches: 17 cm.

Diameter of lateral branches: 3 mm.

Quantity of lateral branches: About 20.

Internode length: 1.5 cm.

Stem:

*Stem shape*.—Round.

*Stem strength*.—Good.

*Stem color*.—RHS Greyed-Orange 165B.

*Texture*.—Pubescent.

FOLIAGE

Leaf:

*Arrangement*.—Alternate, single.

*Leaf shape*.—Elliptic.

*Average length*.—6 cm.

*Average width*.—3 cm.

*Apex*.—Cuspidate.

*Base*.—Cuneate.

*Margin*.—Crenate.

*Texture of top surface*.—Smooth, waxy.

*Texture of bottom surface*.—Smooth, waxy.

*Color*.—Young foliage upper side: RHS Green NN137A. Young foliage under side: RHS Grey-Green 191A. Mature foliage upper side: Spring: RHS Green NN137A. Fall: RHS Red 53A to Red 46C. Mature foliage under side: Spring: RHS Grey-Green 191A. Fall: RHS Greyed-Red 180C.

*Venation*.—Pattern: Pinnate. Color upper side: RHS Yellow-Green 145B. Color under side: RHS Yellow-Green 144D.

*Petiole*.—Average Length: 6 mm. Diameter: 1 mm. Petiole color upper side: RHS Yellow-Green 145B. Petiole color lower side: RHS Yellow-Green 144D. Petiole Texture upper side: Waxy. Petiole Texture lower side: Waxy, slight pubescence.

FLOWER

Natural flowering season: Spring.

Flower arrangement: Corymb.

Inflorescence type and habit: Upright, compound corymb.

Inflorescence height: 2.5 cm.

Inflorescence width: 2.5 cm.

Quantity of flowers per inflorescence: 5-10.

Quantity of flowers per lateral stem: 30-40.

Individual flowers:

*Flower form*.—Rotate.

*Flower shape*.—Radial.

*Flower aspect*.—Upright and outwards.

*Size*.—Diameter: 11 mm. Length: 11 mm. Depth: 5 mm.

Flower other characteristics:

*Persistence*.—Self-cleaning.

*Fragrance*.—Very slight, floral.

Petal:

*Arrangement*.—Whorled.

*Number of petals per flower*.—5.

*Petal fused*.—No.

*Petal shape*.—Orbicular.

*Petal base*.—Attenuate.

*Margin*.—Entire.

*Tip shape*.—Rounded.

*Length*.—4.75 mm.

*Width*.—4 mm.

*Texture*.—Upper: Glabrous. Lower: Glabrous.

Petal color:

*When opening*.—Upper surface: RHS White 155B. Lower surface: RHS White 155B with some Red-Purple 62C flushing.

*Fully opened*.—Upper surface: RHS White 155B. Lower surface: RHS White 155B.

Bud:

*Shape*.—Spherical.

*Length*.—5 mm.

*Diameter*.—4 mm.

*Color*.—RHS White 155B flushed Greyed-Purple 186B.

Calyx:

*Length*.—3 mm.

*Diameter*.—5.25 mm.

Sepals:

*Arrangement*.—Radial.

*Number.*—5.
*Shape.*—Deltate.
*Base.*—Truncate.
*Margin.*—Entire.
*Tip shape.*—Acute.
*Length.*—1 mm.
*Width.*—1 mm.
*Color upper.*—RHS Green 139D.
*Color lower.*—RHS Green 139C.
*Texture, upper side.*—Pubescent.
*Texture, lower side.*—Glabrous.

Peduncle:
*Length.*—7 mm.
*Diameter.*—1 mm.
*Color.*—RHS Yellow-Green 146D.
*Strength.*—Good.
*Texture.*—Glabrous.

REPRODUCTIVE ORGANS

Stamens:
*Number.*—18.
*Filament length.*—4 mm.
*Filament color.*—RHS White 155B.

Anthers:
*Shape.*—Dorsifixed.
*Length.*—1 mm.
*Color.*—RHS Red-Purple 59B.
*Pollen color.*—RHS Brown 200D.
*Pollen amount.*—Scant to moderate.

Pistil:
*Number.*—4.
*Length.*—3 mm.
*Style.*—Length: 1 mm. Color: RHS Yellow-Green 146D.
*Stigma.*—Shape: Fused stigma with 3-5 lobes. Color: RHS Yellow-Green 146D. Ovary Color: RHS Yellow-Green 146D.

OTHER CHARACTERISTICS

Fruit:
*Type.*—Drupe.
*Size.*—5 to 10 cm long, 5 to 8 cm wide.
*Shape.*—Sphere, to slightly ovate.
*Color.*—Near Greyed-Purple N186A.
*Seeds.*—1-3 or none. About 1.5 mm long, 1 mm wide. Colored near Greyed-Purple N187.

Disease/pest resistance: Typical of the species.

Temperature tolerance: The new variety tested to tolerate temperatures between −25° C. to 40° C.

What is claimed is:

1. A new and distinct cultivar of *Aronia* plant named 'UCONNAM012' as herein illustrated and described.

* * * * *